US00PP20165P3

(12) United States Plant Patent
Zaiger et al.

(10) Patent No.: US PP20,165 P3
(45) Date of Patent: Jul. 7, 2009

(54) INTERSPECIFIC TREE NAMED 'AMIGO I'

(50) Latin Name: **Interspecific *Prunus***
Varietal Denomination: Amigo I

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 62 days.

(21) Appl. No.: 11/702,144

(22) Filed: Feb. 5, 2007

(65) Prior Publication Data

US 2008/0189812 P1 Aug. 7, 2008

(51) Int. Cl.
*A01H 5/00* (2006.01)

(52) U.S. Cl. ..... Plt./180
(58) Field of Classification Search ..... Plt./180
See application file for complete search history.

*Primary Examiner*—June Hwu

(57) ABSTRACT

A new and distinct variety of interspecific tree. The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree with a vigorous upright growth habit.
2. Heavy and regular production of fruit.
3. Fruit with an attractive skin color.
4. Fruit having a good balance between acid and sugar with an average Brix of 15.8°.
5. Fruit with good shipping and storage trials.

1 Drawing Sheet

Botanical classification: Interspecific *Prunus* Species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of plums and plumcot, which are known to us, and mentioned herein, are the plums 'Royal Zee' (U.S. Plant Pat. No. 5,486), 'Queen Rose' (non-patented), 'Blue Giant' (U.S. Plant Pat. No. 6,764), 'Crimson Glo' (U.S. Plant Pat. No. 12,856) and the proprietary plumcot '26EB546'.

ORIGIN OF THE VARIETY

The new and distinct variety of interspecific tree, was originated by us from crosses between the following species, (*Prunus salicina*×(*Prunus salicina*×*Prunus armeniaca*)× *Prunus salicina*) in our experimental orchard located near Modesto, Calif. as a first generation cross between the proprietary interspecific seedling with field identification number '276LF278' and 'Crimson Glo' Plum (U.S. Plant Pat. No. 12,856). The seed parent (276LF278) was developed by us from crosses of the following parents, the proprietary plumcot (26EB546), and the plums 'Royal Zee' (U.S. Plant Pat. No. 5,486), 'Queen Rosa' (non-patented) and 'Blue Giant' (U.S. Plant Pat. No. 6,764). The pollen parent was the plum 'Crimson Glo' (U.S. Plant Pat. No. 12,856). A large number of seed from this first generation cross of the proprietary interspecific '276LF278' and 'Crimson Glo' Plum (U.S. Plant Pat. No. 12,856) were grown on their own root in our green house and these seedlings were budded to older trees of 'Nemagaurd' Rootstock (non-patented) in our experimental orchard located near Modesto, Calif., Stanislaus County, to accelerate rapid fruit production for evaluation. Under close and careful observation of these budded seedlings we recognized the desirable fruit characteristics of the present interspecific variety and selected it in 2003 for additional asexual propagation and commercialization.

ASEXUAL REPRODUCTION OF THE VARIETY

Additional asexual reproduction of the new and distinct variety of interspecific tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of interspecific tree ((Plum×Plumcot)× Plum) is of large size, vigorous, upright growth and a productive and regular bearer of medium size fruit with good flavor and eating quality. The fruit is further characterized by having firm flesh, a good balance between acid and sugar with an average Brix of 15.8° and maturing in the early maturity season. The size and maturity of the fruit is relatively uniform throughout the tree. In comparison to its maternal parent (276LF278), the fruit of the new variety has a darker red skin color and is approximately 40 days earlier in maturity. In comparison to the paternal parent 'Crimson Glo' Plum (U.S. Plant Pat. No. 12,856) the fruit of the new variety is similar in size and skin color, has a more yellow flesh and is approximately 28 days earlier in maturity. In comparison to 'Hiromi Red' (U.S. Plant Pat. No. 9,858) the new variety ripens six day earlier than 'Hiromi Red'.

PHOTOGRAPH OF THE VARIETY

The accompanying color photographic illustration shows typical specimens of the foliage and fruit with a flower inset of the present new interspecific variety at 5 years of age. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

*Size.*—Large, pruned to 3 to 3.5 meters in height and width for economical harvesting of fruit. Varies with different cultural practices.

*Vigor.*—Vigorous, growth of 1.5 to 2 meters the first growing season, varies with type and fertility of soil, climatic conditions and cultural practices.

*Form.*—Upright.

*Branching habit.*—Upright, crotch angle approximately 30°, increases with heavy crop load.

*Productivity.*—Productive, thinning and spacing of fruit desirable for market size fruit.

*Bearer.*—Regular, adequate fruit set 3 consecutive years. No alternate bearing observed.

*Fertility.*—Self sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 450 hours at or below 45° F.

Trunk:

*Size.*—Large. Average circumference of 50.8 cm at 20.3 cm above ground on a 5 year old tree.

*Stocky.*—Medium stocky.

*Texture.*—Medium shaggy, becoming rougher with age.

*Color.*—Varies from 7.5YR 3/2 to 10YR 3/2.

Branches:

*Size.*—Medium. Average circumference 16.7 cm at 1.0 meter above ground. Crotch angle approximately 30°, increases with heavy crop load.

*Surface texture.*—New growth smooth, mature growth medium rough, roughness increases with age.

*Lenticles.*—Average number 39 in a 25.8 sq cm area. Average length 3.8 mm. Average width 1.2 mm. Color varies from 7.5YR 5/10 to 10YR 6/8.

*Color.*—New growth varies from 5GY 4/6 to 7.5YR 6/4. Old growth varies from 10YR 4/2 to 2.5Y 4/4, varies with age of growth.

Leaves:

*Size.*—Medium to large. Average length 117.7 mm. Average width 47.1 mm.

*Form.*—Oblanceolate.

*Apex.*—Acuminate.

*Base.*—Cunate.

*Margin.*—Serrate.

*Thickness.*—Medium.

*Surface texture.*—Upper surface relatively smooth, slight indentations over midrib and leaf veins, glabrous. Lower surface relatively smooth, except for small ridges created by midrib and pinnate venations, glabrous.

*Color.*—Upper surface varies from 5GY 3/6 to 7.5GY 3/4. Lower surface varies from 5GY 4/4 to 7.5GY 4/4. Midvein color varies from 2.5GY 6/6 to 5GY 6/6.

*Petiole.*—Average length 18.5 mm. Average width 1.6 mm. Color varies from 5GY 5/8 to 5GY 6/6. Longitudinally grooved. Surface-glabrous.

*Glands.*—Type- globose. Size- small. Average length 0.7 mm. Average diameter 0.4 mm. Average number- 2, varies from 1 to 3. Located primarily on lower portion of leaf blade and upper portion of petiole. Color varies from 5GY 6/6 to 5GY 5/6.

Flower buds:

*Size.*—Medium. Average length 9.2 mm. Average diameter 6.3 mm.

*Hardiness.*—Hardy with respect to California winters.

*Form.*—Conical, becoming slightly elongated before opening.

*Pedicel.*—Size- medium. Average length 6.9 mm. Average width 0.8 mm. Color varies from 10Y 7/6 to 2.5GY 6/6. Surface- glabrous.

*Color.*—N 9.5/ (white).

*Number of buds per spur.*—Average number 4, varies with age of spur.

Flowers:

*Size.*—Medium. Average height 12.0 mm. Average diameter 19.2 mm.

*Petals.*—Number 5, alternately arranged to sepals. Size- medium. Average length 9.5 mm. Average width 8.8 mm. Form- orbicular, narrows slightly at point of attachment. Margin- sinuate. Both surfaces glabrous. Color- N 9.5/ (white).

*Sepals.*—Number 5, alternately arranged to petals. Shape- triangular, apex rounded. Size- small. Average length 3.5 mm. Average width 2.9 mm. Both surfaces glabrous. Color- upper surface varies from 2.5GY 6/6 to 5GY 6/6. Lower surface varies from 2.5GY 6/6 to 5GY 5/6.

*Stamens.*—Average number 36 per flower. Average filament length 7.2 mm. Filament color N 9.5/ (white). Anther color varies from 10R 5/8 to 2.5YR 5/6.

*Pollen.*—Self sterile, pollinator required. Color varies from 2.5Y 8/12 to 5Y 8/10.

*Pistil.*—Normally one. Surface- glabrous. Average length 9.5 mm. Position of stigma, approximately same height as anthers. Color varies from 2.5GY 7/6 to 2.5GY 6/6.

*Fragrance.*—Moderate.

*Blooming period.*—Date of First Bloom Feb. 18, 2006. Date of Petal Fall Feb. 27, 2006, varies slightly with climatic conditions.

*Color.*—N 9.5/ (white).
*Number flower per flower bud.*—Average number 2, varies from 1 to 4.
*Pedicel.*—Average length 7.5 mm. Average width 0.9 mm. Color varies from 10Y 7/6 to 2.5GY 6/6. Surface- glabrous.

Fruit:
*Maturity when described.*—Firm ripe.
*Date of first picking.*—Jun. 15, 2006.
*Date of last picking.*—Jun. 23, 2006, varies slightly with climatic conditions.
*Size.*—Medium. Average diameter axially 47.8 mm. Average transversely in suture plane 57.9 mm. Average weight 117.4 grams, varies slightly with fertility of the soil, amount of thinning and climatic conditions.
*Form.*—Globose.
*Suture.*—Nearly smooth, extends from base to apex.
*Ventral surface.*—Very slightly lipped, nearly smooth.
*Apex.*—Nearly rounded, slight point on some fruit.
*Base.*—Retuse.
*Cavity.*—Rounded to slightly elongated in suture plane. Average depth 5.6 mm. Average diameter 11.5 mm.

Stem:
*Size.*—Small to medium. Average length 11.1 mm. Average diameter 1.7 mm.
*Color.*—Varies from 10Y 5/6 to 7.5Y 5/6.

Flesh:
*Ripens.*—Relatively even, slightly earlier near apex.
*Texture.*—Firm, meaty.
*Fibers.*—Few, small, tender.
*Firmness.*—Good, comparable to other commercial interspecific varieties.
*Aromatic.*—Slight.
*Amydgalin.*—Undetected.
*Eating quality.*—Good.
*Flavor.*—Good.
*Juice.*—Moderate amount, enhances flavor.
*Brix.*—Average Brix 15.8°, varies slightly with amount of fruit per tree and climatic conditions.
*Color.*—Yellow to red, varies from 5Y 8/8 to 7.5R 4/8. Pit cavity varies from 2.5Y 5/6 to 2.5Y 6/6.

Skin:
*Thickness.*—Medium.
*Surface.*—Relatively smooth, very slightly waffled.
*Bloom.*—Light, completely covered.
*Tendency to crack.*—None.
*Color.*—Ground color varies from 2.5Y 8.5/4 to 2.5Y 8.5/6. Overspread with 2.5R 2/4 to 5R 2/6.
*Tenacity.*—Tenacious to flesh.
*Astringency* .—Undetected.

Stone:
*Type.*—Clingstone.
*Size.*—Small to medium. Average length 18.2 mm. Average width 18.6 mm. Average thickness 12.1 mm.
*Form.*—Globose.
*Base.*—Varies from flat to rounded.
*Apex.*—Varies from round to very slight point. Average length 0.2 mm.
*Surface.*—Slightly pitted throughout, one very shallow groove on each side of suture.
*Sides.*—Unequal, with one side extending further from suture plane.
*Ridges.*—A very small narrow ridge on each side of suture.
*Tendency to split.*—None.
*Color.*—Varies from 10YR 6/6 to 10YR 5/8.

Kernel:
*Form.*—Ovate.
*Taste.*—Bitter.
*Viability.*—Difficult, embryo only partially developed.
*Size.*—Small. Average length 10.8 mm. Average width 9.5 mm. Average depth 5.9 mm.
*Skin.*—Color varies from 5Y 9/4 to 5Y 8.5/6 when dry.

Use: Dessert. Market- local and long distance.

Keeping quality: Good, held firm in cold storage for 3 weeks at 38° to 42° F. without internal breakdown of flesh or appreciable loss of flavor.

Shipping quality: Good, minimal flesh bruising or skin scarring during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

I claim:

1. A new and distinct variety of interspecific tree, substantially as illustrated and described.

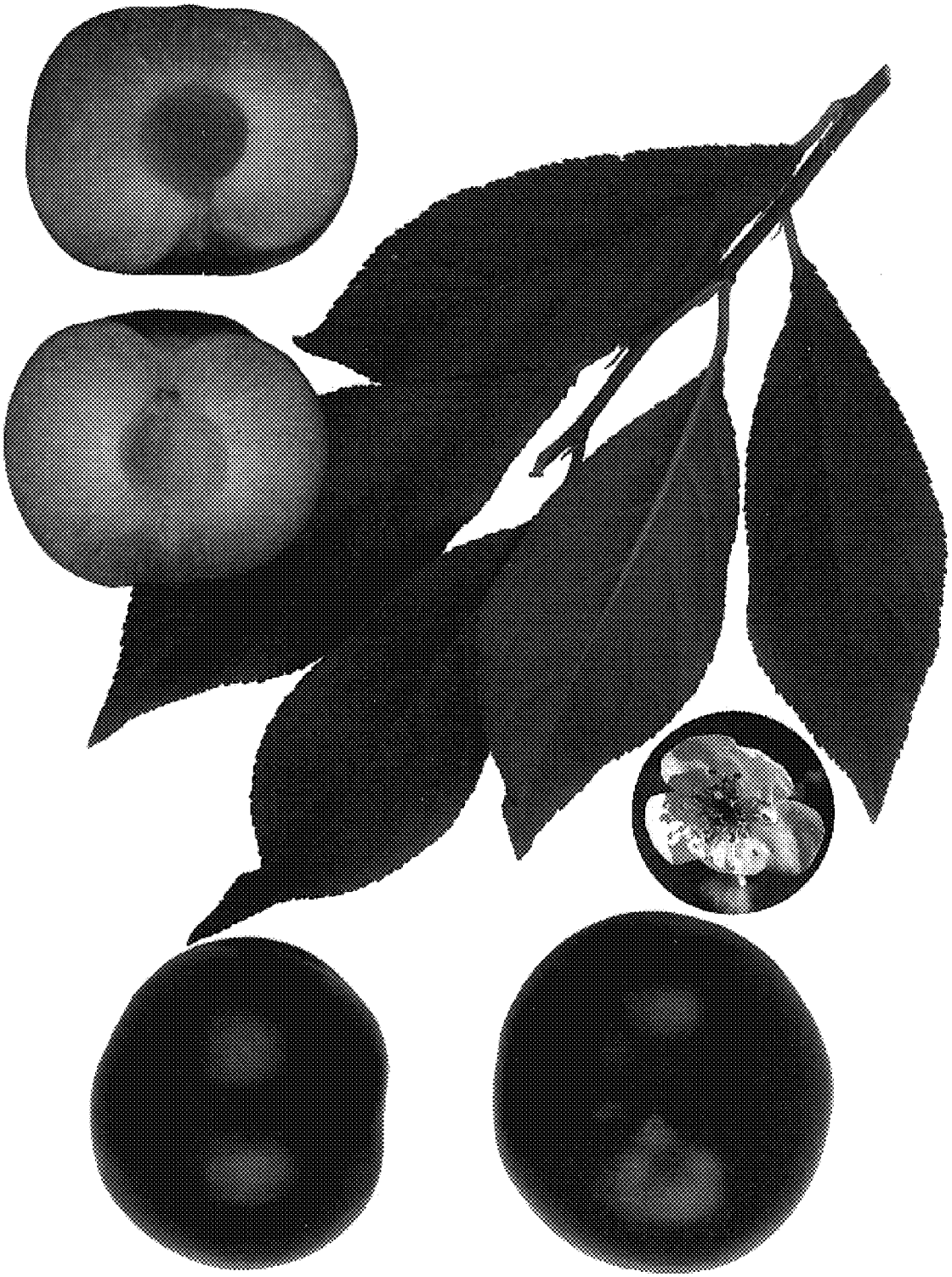

* * * * *